United States Patent [19]
Duret et al.

[11] Patent Number: 5,237,998
[45] Date of Patent: Aug. 24, 1993

[54] METHOD OF CORRELATING THE THREE-DIMENSIONAL IMAGES OF HUMAN ORGANS AND DEVICE FOR IMPLEMENTATION OF THE METHOD

[75] Inventors: Francois Duret, Les Grand-Lemps; Jean-Louis Blouin, Vienne; Gilles Dechellete, Sainte-Foy-les-Lyons, all of France

[73] Assignee: Sopha Bioconcept S.A., Vienne, France

[21] Appl. No.: 548,947

[22] PCT Filed: Nov. 17, 1989

[86] PCT No.: PCT/FR89/00594
§ 371 Date: Jul. 27, 1990
§ 102(e) Date: Jul. 27, 1990

[87] PCT Pub. No.: WO90/05483
PCT Pub. Date: May 31, 1990

[30] Foreign Application Priority Data
Nov. 18, 1988 [FR] France .................. 88 15483

[51] Int. Cl.⁵ .............................. A61B 6/02
[52] U.S. Cl. .................................. 128/665
[58] Field of Search ............ 395/120, 124, 127; 356/376; 128/665; 364/413.13, 413.28, 413.15, 413.22, 413.19; 433/213, 214

[56] References Cited

U.S. PATENT DOCUMENTS

| | | | |
|---|---|---|---|
| 4,611,288 | 9/1986 | Duret et al. | 128/665 |
| 4,729,098 | 3/1988 | Cline | 359/124 |
| 4,742,464 | 5/1988 | Duret et al. | 433/214 |
| 4,885,688 | 12/1989 | Crawford | 395/127 |
| 4,964,770 | 10/1990 | Steinbichler | 433/214 |
| 4,977,505 | 12/1990 | Pelizzari | 364/413.13 |
| 5,016,639 | 5/1991 | Allen | 364/413.13 |
| 5,027,281 | 7/1991 | Rekow et al. | 364/413.28 |
| 5,038,302 | 8/1991 | Kaufman | 395/124 |
| 5,070,454 | 12/1991 | Griffith | 364/413.13 |

OTHER PUBLICATIONS

Ueda, Ken, "Three-Dimensional Analysis for Prediction and Assessment of Mandibular Movement in Orthognathic Surgery in the Ramus", J. max-fac., Surg., 11, (1983), pp. 216-226.

Primary Examiner—Lee S. Cohen
Assistant Examiner—Samuel Gilbert
Attorney, Agent, or Firm—Herbert Dubno

[57] ABSTRACT

The three-dimensional correlation of images of a human organ, especially dental arcades, uses an impression in the occlusive position, providing a reference in the form of three mutually spaced reference points. Three-dimensional views are taken of the impression and the points and views are also taken with the impression removed. Using the images of the reference points as a basis, the sets of views are then correlated to bring them into a single referential system.

9 Claims, 2 Drawing Sheets

METHOD OF CORRELATING THE THREE-DIMENSIONAL IMAGES OF HUMAN ORGANS AND DEVICE FOR IMPLEMENTATION OF THE METHOD

CROSS REFERENCE TO RELATED APPLICATIONS

This application is a national phase of PCT/FR 89/00594 filed Nov. 17, 1989 and based upon French national application 88 15483 of Nov. 18, 1988 under the International Convention.

FIELD OF THE INVENTION

The present invention relates to a method of correlating three-dimensional images of human organs and to a device for the implementation of the method.

BACKGROUND OF THE INVENTION

Various methods exist for imaging the shape of an internal and external human organ.

The first consists in using an impression paste of greater or lesser elasticity and in reconstructing the part by plaster casting in order to obtain the complete reproduction of said organ.

A second method described by Moshabac in 1977 (U.S. Pat. No. 4,182,312) and then by Becker (U.S. Pat. No. 4,411,626) consists in micro-tracing the surface being studied and, where appropriate, reconstructing it using a micro-profiler.

A third method consists in taking an X-ray or tomo-densitometric reading, then in repositioning each section as a function of the position of the X-ray analysis receivers and sensors.

A fourth method consists in using the NMR principle (nuclear magnetic resonance) or MRI principle (MR imaging), known methods which have been widely described and permit reconstruction of the part using a numerically controlled micro-profiler (Information dentaire, September 1988).

Finally, a new method described in a series of previous documents uses stereoscopic methods (Rooder) or moiré effect methods (Duret) and makes it possible to take a three-dimensional reading of the objects photographed.

This last method, introduced very recently in dentistry, makes it possible to form an image, but does not afford the possibility of correlating various images in order to obtain an overall view of the part which is the subject of the study.

In particular, the only means used in order to correlate views presupposes the fixing of the object analyzed and of the camera in known positions of the computing and analysis center. Thus, it is relatively common nowadays to effect a rotation of the object facing the analysis camera. Such a technique is difficult to implement in the case of the imaging of a part of the jaw of a subject, in the case of dentistry.

OBJECTS OF THE INVENTION

The object of the present invention is to provide a method of and a device for the correlation of a set of three-dimensional dental or medical views of an object or to correlate several objects which may themselves have formed the subject of a correlation, without knowing a priori the position of the object and of the camera at the computer level.

SUMMARY OF THE INVENTION

To this end, the method to which the invention relates consists in affixing or locating, on the organ or on the environment of the organ whose imaging is to be effected, three reference points chosen so as all to be visible on the views obtained by the various imagings, and in carrying out a calculation of correlation of the views obtained by the various imagings in order to bring them into a single referential system, taking into account the three reference points.

This method advantageously consists in carrying out, during the correlation operation, a smoothing of the points which is associated with the apparent densities of each view, omitting from the latter any zone in which the density of the points is below a predetermined value.

In accordance with one aspect of this invention, this method consists in using a support for each reference point, consisting of a surface, if appropriate delimited by a contrast frame, making it possible to site the distance of the point relative to the camera by a statistical estimation of the value of this distance on a number of points which is higher, the greater the surface, then in determining the center of the reference point by a progressive skeletonization operation.

Advantageously, and in order to avoid the disadvantages due to the precise determination of a point on a glancing plane, each surface associated with a reference point consists of a surface of simple geometric shape making it possible to obtain by calculation an apparent or actual characteristic point which can serve as a basis for correlation.

According to one possibility, the surface associated with a reference point consists of a sphere, whose reference point is the center.

This solution is advantageous, since a sphere is a surface which is easy to recognize and has the same shape and the same surface whatever the angle at which it is viewed.

The method advantageously consists in carrying out an automatic determination of the reference points by prior recognition of the shape of the surfaces associated with the three points, which eliminates the risks of error in manual correlation.

In fact, the determination of the coordinates of the image does not depend on the correlation points. It is thus possible to establish the position of a sphere relative to the optical center of the camera. Knowing this value, it is possible to describe the enlargement and consequently the sphericity and the center of the theoretical sphere.

Moreover, a rapid calculation carried out on these points before calculating the image informs the operator immediately of the quality of the images (blurring, coding . . . ).

In accordance with a preferred feature of the matter, the reference points are arranged on the periphery of the zone whose imaging is to be effected, which minimizes the correlation error, since the lever arm effect is more reduced in the central zone than in the peripheral zone.

In the case of its application in dentistry, the method consists in using, as reference points, points characteristic of the image, such as summits of the cusps or grooves.

It should be noted that detection using three points affords a number of other advantages, namely:

The manual indication of a single point, and always the same point, permits direct and automatic numbering of the other points (for example in clockwise direction). Thus, the practitioner will be able to mark the vestibular point in the mouth.

The fact of indicating at least one point can enable the software to estimate the shape which it has to recover automatically and its enlargement approximately (the zone of definition limits the variations: depth of field).

When the correlation of images of a jaw is to be carried out, one solution consists in using three reference points on the maxilla, and three reference points on the mandible, which permits correlation of the images of the maxilla and of the images of the mandible, respectively.

At the moment when the two jaws approach, one or more reference points, for example situated on the inner side of the jaw, are masked. In order to promote the stability of the correlations, an additional point will be placed in the upper vestibule and another will be placed in the lower vestibule. These two points ensure the restoration of two groups of three reference points above and below. Although this method is rational and permits a reduction in the number of correlation points, while at the same time making it possible to carry out intra-object and inter-object correlations, it remains complex.

In one of its modes of implementation, the method according to the invention makes it possible to carry out correlations between maxilla and mandible in a simple manner.

To this end, it consists in producing an impression of the antagonist teeth, facing the cut zone, in the case of the production of a prosthesis, in placing this impression on the zone of the cut tooth and on the surrounding teeth, in placing three reference points on this zone, these three points serving, on the one hand, for the correlation of the antagonist teeth, taking into consideration the impression of the latter, and, on the other hand, for the correlation of the teeth of the arch where the tooth is cut, after removal of the element comprising the impression.

It is thus possible to limit oneself to three reference points for the correlation of any organ, even if a correlation with a neighboring organ is necessary.

A device for the implementation of this method comprises a support for the reference points which can be fixed in a removable manner on the organ whose image is to be supplied.

In accordance with one embodiment of this device, the surfaces with which the reference points are associated are fixed, in the case of an application in dentistry, on two arms which are fixed to an elastic cradle which is able to exert a pressure on at least one tooth, these two arms being arranged on the side of the lingual and vestibular surfaces.

In accordance with another embodiment, the surfaces with which the reference points are associated are fixed to two separate arms which, designed to be arranged on the lingual and vestibular surfaces respectively, are equipped with fixation means, such as means for adhesive bonding.

In accordance with another advantageous embodiment to be used for producing the optical image of a large section of the mouth, the device supporting the reference points comprises a bar extending along the lingual and vestibular surfaces of the teeth of a jaw, fitted with means for fixation on said jaw, for example by engagement of wedges between two teeth, and on which there are mounted, sliding and capable of being locked in the desired position, rods supporting the surfaces with which the various reference points are associated. The locking effect can be obtained by a screw clamping.

BRIEF DESCRIPTION OF THE DRAWING

The invention will be fully understood anyway from the description which follows, and in which reference is made to the attached diagrammatic drawing showing, by way of non-limiting examples, several embodiments for the implementation of this method.

SPECIFIC DESCRIPTION

Figure 1:
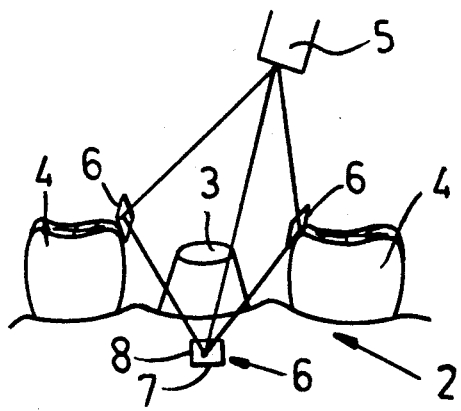
FIG. 1 is a highly diagrammatic view of an arrangement used for the correlation of a zone of a jaw.

FIG. 1 shows, in a very diagrammatic manner, a part 2 of a dental arch comprising a stump 3 situated between two healthy teeth 4. In order to carry out several optical imagings of this zone at different angles, using an analysis camera 5, it is necessary to position, preferably on the periphery of the zone comprising the stump 3, three reference points 6 each of which belongs to a surface 7 bordered by a contrast color frame 8. The three points 6 are, as has been indicated above, arranged around the stump in such a way as to surround the latter.

Figure 2:
FIG. 2 is a perspective view of a tooth.

FIG. 2 shows a tooth whose reference points 6 are formed by the cusps and the groove.

Figure 3:
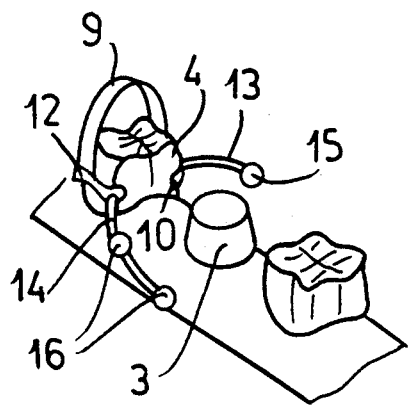
FIGS. 3 to 5 are three perspective views of three devices for supporting reference points.

FIG. 3 shows a device consisting of a clamp 9 made of an elastic material and designed to clamp around a tooth 4. This clamp has two hooks 10, 12 bearing against the lingual and vestibular surfaces of the tooth and bearing two arms 13, 14 respectively. The arm 13 is fitted with a sphere 15 permitting determination of one reference point, while the arm 14 is fitted with two spheres 16 permitting the determination of two other reference points.

Figure 4:
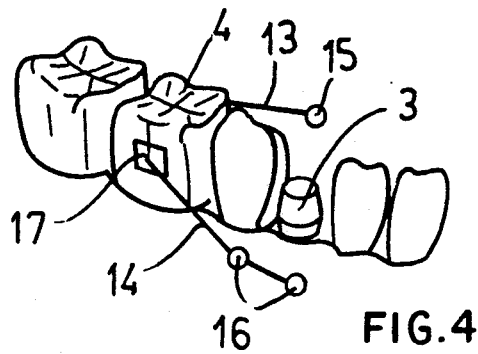

FIG. 4 shows a variant in which the arms 13 and 14 bearing the spheres 15 and 16, respectively, are each fitted with an adhesive patch 17 designed to be fixed on the surface of a tooth, the lingual surface or vestibular surface respectively.

Figure 5:
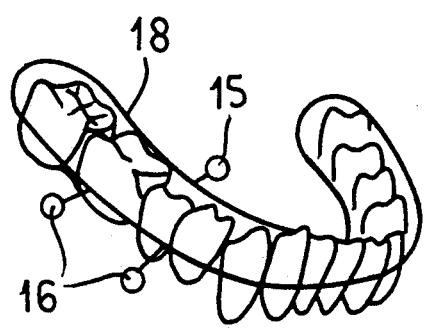
Figure 6:
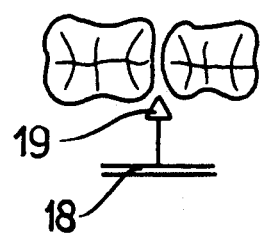
FIGS. 6 and 7 are two detail views of the device in FIG. 5.

FIG. 5 shows a device comprising a closed bar 18 designed to pass along the lingual and vestibular surfaces and fixed with respect to the jaw for example by means of wedges 19 engaged between two teeth, as shown in FIG. 6.

Figure 7:
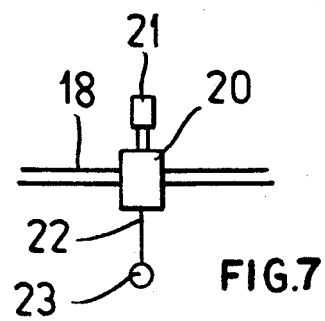
Figure 8:
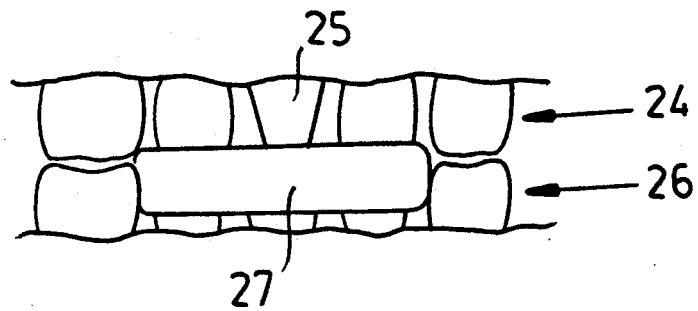
FIGS. 8 to 12 show, very diagrammatically, a device permitting the correlation of images between the two parts of the jaw of a subject.
Figure 9:
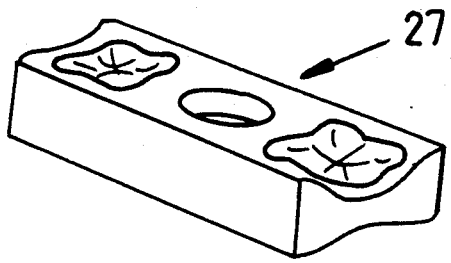
Figure 10:
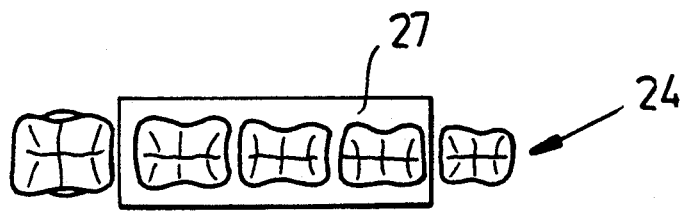

As shown in FIG. 7, riders 20 are mounted on the bar 18 in a sliding manner, with the possibility of being locked by a screw 21, each of the riders 20 bearing a rod 22 whose free end is fitted with a sphere 23 designed to establish a reference point.

Figure 11:
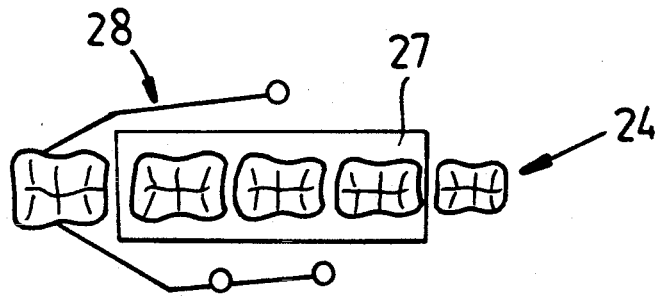

FIGS. 8 to 12 show, diagrammatically, various stages in a procedure permitting the correlation of the image of the two parts of a jaw, namely an upper part 24, comprising a cut tooth 25 designed to receive a prosthesis, and a lower part 26. An impression is taken of the lower part 26 of the jaw using a paste 27, by the "bite"

technique. The paste component 27 is then positioned on the part 24 of the jaw comprising the stump 25. A system 28 comprising reference points, consisting for example of the system shown in FIG. 3, is placed on this part of the jaw. As shown in FIG. 11, a correlation is then carried out, taking into account the hollow part of the impression 27 which is the negative of the part 26 of the antagonist jaw in the prosthesis zone.

Figure 12:
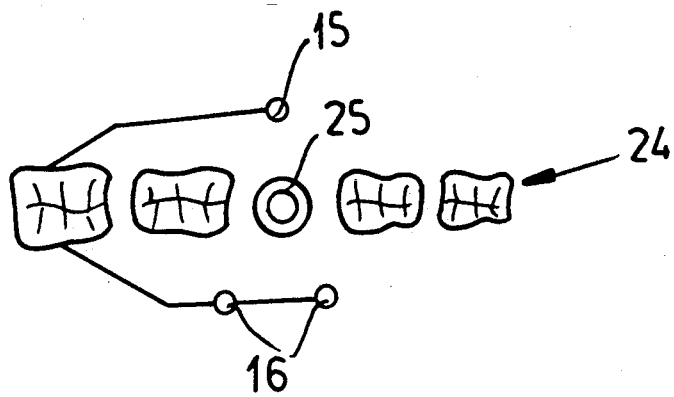

The paste component 27 is then removed, and, as is shown in FIG. 12, optical imaging of the prosthesis zone itself is then carried out. It is worth noting that the correlation at each part of the jaw and between the two parts of the jaw is carried out using the same reference points.

As is clear from the foregoing, the invention brings a great improvement to the existing technique, by providing a method of simple design, permitting the correlation of three-dimensional images of human organs, of great reliability and eliminating all difficulties for the practitioner.

It goes without saying that the invention is not limited to the modes of application of this method nor to the embodiments of this device as described hereinabove solely by way of example; on the contrary, it includes all the variant embodiments, and, therefore, in particular the form of the surfaces from which the reference points are defined could be different from a plane or a sphere, without thereby departing from the scope of the invention.

We claim:

1. A method for correlating three-dimensional images of human organs able to move from an open condition to an occlusive condition, comprising the steps of:
    (a) producing an impression in the occlusive condition of a first organ and a second organ, by using a paste capable of being impressed by occlusing of said first and said second organs;
    (b) placing said impression on said first organ whereby hollow parts are formed in said impression by occlusion of said second organ thereagainst;
    (c) locating in a fixed and visible condition in a region of said first organ a set of three mutually spaced apart reference points;
    (d) taking first three-dimensional views of the hollow parts of the impression corresponding to the negative of said second organ with images of said three reference points visible on said first views;
    (e) removing said impression from said first organ;
    (f) taking second three-dimensional views of said first organ with said three reference points visible on said second views; and
    (g) carrying out a calculation of correlation of said first views and said second views to bring them into a single referential system defined by said three reference points.

2. The method of claim 1 wherein each reference point is supported by a surface, said surface bearing a contrast frame with a border or a contour, comprising further the steps of:
    evaluating a position and a distance of an analysis camera relative to a reference point, taking into account an area of a corresponding surface and a contour of a corresponding frame as viewed by said analysis camera; and
    determining a center of the reference point by progressive skeletonization operation.

3. The method of claim 2 wherein a surface associated with a reference point is at least partially spherical, the center of said at least partially spherical surface being a respective one of said reference points.

4. The method of claim 2 wherein a shape of said surface is of such a simple geometry that a characteristic point thereof is obtained by calculation.

5. The method of claim 2 wherein each surface associated with a reference point has a different shape, comprising the steps of:
    recognizing a shape of each said surface;
    determining each individual reference point; and
    automatically numbering each point in a given direction.

6. The method of claim 1 wherein said set of three reference points comprises a first arm bearing two reference points and a second arm bearing a third reference point.

7. The method of claim 1, further comprising the steps of:
    comparing apparent densities of points of each view with a predetermined value; and
    omitting from the three-dimensional images zones corresponding to apparent densities lower than said predetermined value.

8. The method of claim 1 wherein the set of three reference points is affixed on an outer periphery of said first organ.

9. The method of claim 1 wherein the three-dimensional images of human organs are viewed by an analysis camera movable relatively to said human organs, an output of said analysis camera being directly fed into a computer.

* * * * *